(12) United States Patent
Azizzadeh

(10) Patent No.: US 12,121,570 B2
(45) Date of Patent: *Oct. 22, 2024

(54) TREATMENT OF STRESS DISORDERS USING ACETYLCHOLINE RELEASE INHIBITING NEUROTOXIC PROTEINS TO REDUCE STRESS LEVELS

(71) Applicant: Babak Azizzadeh, Beverly Hills, CA (US)

(72) Inventor: Babak Azizzadeh, Beverly Hills, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/464,583

(22) Filed: Sep. 11, 2023

(65) Prior Publication Data

US 2023/0414729 A1    Dec. 28, 2023

Related U.S. Application Data

(63) Continuation of application No. 16/736,285, filed on Jan. 7, 2020, now Pat. No. 11,752,201.

(60) Provisional application No. 62/789,126, filed on Jan. 7, 2019.

(51) Int. Cl.
*A61K 38/48* (2006.01)
*A61K 9/00* (2006.01)
*A61P 25/22* (2006.01)

(52) U.S. Cl.
CPC ........ *A61K 38/4893* (2013.01); *A61K 9/0019* (2013.01); *A61P 25/22* (2018.01)

(58) Field of Classification Search
CPC .... A61K 9/0019; A61K 38/4893; A61P 25/22
See application file for complete search history.

(56) References Cited

U.S. PATENT DOCUMENTS 11,752,201 B2 * 9/2023 Azizzadeh .............. A61P 25/24
424/94.67
2020/0215170 A1    7/2020 Azizzadeh

* cited by examiner

*Primary Examiner* — Ruth A Davis
(74) *Attorney, Agent, or Firm* — Cislo & Thomas, LLP

(57) ABSTRACT

Herein disclosed are improved methods for treating stress disorders, such as Post-Traumatic Stress Disorder and perceived stress, by administration of acetylcholine release inhibitors, such as neurotoxic proteins (e.g., a botulinum toxin), to a patient at specific locations and amounts.

17 Claims, No Drawings

TREATMENT OF STRESS DISORDERS USING ACETYLCHOLINE RELEASE INHIBITING NEUROTOXIC PROTEINS TO REDUCE STRESS LEVELS

CROSS-REFERENCE TO RELATED APPLICATION

This application is a continuation application of U.S. patent application Ser. No. 16/736,285, filed Jan. 7, 2020, which claims the benefit of U.S. Provisional Patent Application No. 62/789,126, filed on Jan. 7, 2019, the contents of which are incorporated herein by reference in their entirety.

TECHNICAL FIELD

The present disclosure relates generally to methods to treat stress disorders in patients. More particularly, embodiments of the present disclosure relate to the use of neurotoxins to manipulate facial muscle activity to alleviate one or more symptoms of stress in a patient.

BACKGROUND

It is suggested that a connection exists between an individual's stress levels and their facial muscle activity. For example, patients suffering from stress disorders such as chronic stress and post-traumatic stress disorder ("PTSD") often have increased activity of the facial muscles associated with tension (e.g., masseter and temporalis), anger (e.g., corrugators and procerus), and frowning (e.g., depressor anguli oris and platysma). Moreover, temporomandibular joint ("TMJ") complications (e.g., chronic teeth grinding or jaw clenching) often arise from increased facial muscle activity induced by high levels of stress. Lobbezoo F., van der Zaag J., Naeije M., 33(4) J. OR. REHAB. 293-300 (2006). This connection was once believed to be influenced solely by the individual's stress. However, recent research examining the relationship between an individual's stress level and their facial muscle activity suggests that the connection is actually more reciprocal in nature. See Kraft and Pressman, *Grin and Bear it: The Influence of Manipulated Facial Expression on the Stress Response,* 23(11) APS 1372-78 (2012).

Presently, there are no effective treatment methods designed to manipulate a person's facial muscle activity to reduce their stress levels. Current treatment methods for individuals suffering stress disorders are focused solely on helping the individual cope with their stress, mostly through the use of behavior modulating drugs (e.g., anxiolytics, antidepressants, sleeping pills, etc.). Such treatment methods are often ineffective, short-lived, or have imperfect patient compliance. Moreover, long-lasting coping methods, such as long-term antidepressant use, are often associated with adverse side effects. Accordingly, it is the goal of the present disclosure to provide a more reliable and efficacious method of reducing stress and anxiety in patients experiencing stress disorders by manipulating their facial muscle activity.

SUMMARY

Embodiments of the invention described herein are directed to methods of treating stress in a patient by manipulating their facial muscle activity through local administration of an acetylcholine release inhibiting neurotoxin.

In embodiments of the invention, the methods described herein may be used to treat stress, including alleviating one or more symptoms of stress. In certain embodiments of the invention, the stress is a perceived stress. In certain embodiments of the invention, the stress is post-traumatic stress disorder ("PTSD"). In certain embodiments of the invention, the stress is acute stress disorder ("ASD").

In embodiments of the invention, the acetylcholine release inhibiting neurotoxin to be administered to alleviate one or more symptoms of stress is a *Clostridial* toxin. In certain embodiments of the invention, the *Clostridial* toxin used may be a botulinum toxin, such as a botulinum toxin serotype A, B, C, D, E, F or G. In embodiments of the invention, the botulinum toxin may be botulinum toxin type A, type B, type C, type D, type E, type F, or type G. In certain embodiments of the invention, the botulinum toxin may be a recombinantly made, (i.e., produced by *E. coli*), modified (altering at least one amino acid), or a derivative or fragment thereof.

In embodiments of the invention, the methods of treating stress described herein include administering an effective amount of a *Clostridial* toxin to one or more muscles in a face of a patient. In certain embodiments of the invention, administration of an effective amount of the *Clostridial* toxin is by local injection. In certain embodiments of the invention, administration of an effective amount of the *Clostridial* toxin may be by transdermal route (i.e., by application of a *Clostridial* toxin in a cream, patch or lotion vehicle), subdermal route (i.e., subcutaneous or intramuscular), or by intradermal route of administration.

In embodiments of the invention, the effective amount of a *Clostridial* toxin, such as a botulinum toxin, to be administered is between about 1 unit and about 3,000 units per local injection. In certain embodiments of the invention, the effective amount is between about 1 unit and about 1,000 units. In certain embodiments of the invention, the effective amount is between about 5 units and about 60 units per local injection.

In embodiments of the invention, local administration of an effective amount of a *Clostridial* toxin, such as a botulinum toxin, effectively prevents or alleviates one or more symptoms of stress by manipulating the activity of one or more facial muscles to a affect facial expression.

In embodiments of the invention, local administration of an effective amount of a *Clostridial* toxin, such as a botulinum toxin, effectively prevents or alleviates one or more symptoms of stress by manipulating the activity of one or more facial muscles in a manner that relieves tension in the muscle or group of muscles.

In embodiments of the invention, a targeted fixed injection paradigm for administration of the *Clostridial* toxin that is directed to a specific set of muscles in all patients with a specific minimum number of injection sites is provided. In certain embodiments of the invention, additional/optional administrations of alternative *Clostridial* toxins to specific sites of selected muscles are provided.

In embodiments of the invention, a *Clostridial* toxin is administered to one or more muscles in a face of a patient to manipulate their activity. In certain embodiments of the invention, facial muscles that may be targeted include, for example, the orbicularis oculi, nasalis, levator labii superioris alaeque nasi, depressor labii inferioris, procerus, auriculars, zygomaticus major, zygomaticus minor, buccinator, occipitofrontalis (including the frontal and occipital belly), corrugator supercilii, risorius, depressor anguli oris, orbicularis oris, mentalis, temporalis, medial pterygoid, lateral pterygoid, platysma, and the masseter.

In certain embodiments of the invention, the methods for treating stress in a patient described herein include administering an effective amount of a *Clostridial* toxin, such as a botulinum toxin, to one or more muscles in a face of a patient to manipulate the muscle's activity. In certain embodiments of the invention, treating stress in a patient includes administering an effective amount of a botulinum toxin to one or more facial muscles in a face of a patient, wherein the facial muscle's activity is manipulated in a manner to affect a facial expression. In certain embodiments of the invention, treating stress in a patient includes administering an effective amount of a botulinum toxin to one or more muscles in a face of a patient, wherein the facial muscle's activity is manipulated in a manner to relieve tension in the muscle.

In certain embodiments of the invention, the stress that may be treated through administering an effective amount of a *Clostridial* toxin, such as a botulinum toxin, into one or more muscles in a face of a patient to manipulate their facial muscle activity includes, for example, PTSD. In certain embodiments of the invention, the stress that may be treated through administering an effective amount of a botulinum toxin into one or more muscles in a face of a patient to manipulate their facial muscle activity includes, for example, perceived stress.

In certain embodiments of the invention, treating or alleviating stress in a patient includes manipulating the activity of one or more muscles in a patient's face by administering an effective amount of a *Clostridial* toxin, such as a botulinum toxin, for example botulinum toxin type A, to affect a facial expression. In certain embodiments of the invention, treating or alleviating stress in a patient includes manipulating the activity of one or more muscles in a patient's face by administering an effective amount of a *Clostridial* toxin, such as a botulinum toxin, for example botulinum toxin type A, to relive tension in the muscle. In certain embodiments of the invention, the facial muscles whose activity may be influenced by manipulation include the corrugator supercilii, procerus, depressor supercilii, orbicularis oculi, *frontalis*, masseter, depressor anguli oris, temporalis, and the platysma. In certain embodiments of the invention, administration of the botulinum toxin is by local injection. In certain embodiments, the amount of botulinum toxin type A to be injected ranges from about 1 unit to about 50 units per injection.

Additional and alternative embodiments will be apparent from the following Detailed Description and Claims.

DETAILED DESCRIPTION OF THE INVENTION

Definitions

It is understood that the present invention is not limited to the particular methodologies, protocols, fillers, and excipients, etc., described herein, as these may vary. It is understood that the terminology used herein is used for the purpose of describing particular embodiments only, and it not intended to limit the scope of the present invention. It must be noted that as used herein and in the appended claims, the singular forms "a," "an," and "the" include the plural reference unless the context clearly dictates otherwise. Thus, for example, a reference to a "neurotoxin" is a reference to one or more neurotoxins and includes equivalents thereof known to those skilled in the art and so forth.

Unless defined otherwise, all technical and scientific terms used herein have the same meanings as commonly understood by one of ordinary skill in the art to which this invention belongs. Specific methods, devices, and materials are described, although any methods and materials similar or equivalent to those described herein can be used in the practice or testing of the present invention. All references cited herein are incorporated by reference herein in their entirety.

As used herein, the terms "neurotoxin" or "toxin" refer to a neurotoxic protein produced by one or more members of the *Clostridium* genus of bacteria. Members of the genus include, but are not limited to, the following species: *Clostridium botulinum, Clostridium butyricum, Clostridium tetani, Clostridium perfringens, Clostridium sporogenes, Clostridium leptum, Clostridium difficile* and *Clostridium beratti*.

The term "about," when located before a dosage amount or dosage range of a specific ingredient, refers to an amount or range closely above and/or closely below that stated amount or range that does not manifestly alter the therapeutic effect of the specific ingredient from the stated amount or range and is meant to encompass at least all equivalents of that amount. Thus, the term "about" before a specific value may define a range from about the specific value minus as least 10% or at least 20% to the specific value plus at least 10% or at least 20% of the specific value.

The terms "alleviate" or "alleviating" means a reduction in the occurrence of stress or of a symptom of stress, chronic stress, and/or PTSD. Thus, alleviating includes some reduction, significant reduction, near total reduction, and total reduction. An alleviating effect may not appear clinically for between 1 to 7 days after administration of a *Clostridium* toxin (or a similar alternative) to a patient or sometime after.

As used herein, an "effective amount" refers to the amount of material that is effective to prevent, alleviate, or ameliorate one or more symptoms of a disease or medical condition. The effective amount will vary depending on the compound, the disorder or condition and its severity and the age, weight, etc., of the subject being treated. For example, an effective amount is an amount sufficient to effectuate a beneficial or desired clinical result. The effective amounts can be provided all at once in a single administration or in partial or fractional amounts that provide the effective amount in more than one administrations. The precise determination of what would be considered an effective amount may be based on factors individual to each subject, including their size, age, injury, and/or disorder or condition being treated, and the amount of time since the disorder or condition has begun. One skilled in the art will be able to determine the effective amount for a given subject based on these considerations which are routine in the art.

The term "dosage form," as used herein, may be the form in which the dose is administered to the subject or patient. The drug or supplement is generally administered as part of a formulation that includes nonmedical agents. The dosage form has unique physical and pharmaceutical characteristics. Dosage form may include for example, a liquid composition, a concentrated powder, a dissolvable form, a granulated form, and a pellet form. Dosage form may also include a subdermal implant, a transdermal patch, an injectable form, or an adhesive tablet.

The term "administrable" refers to a composition that is able to be given to a subject. Likewise, the term "administering" refers to the act of giving a composition to a subject or otherwise making a composition available to a subject or the subject taking the composition.

The term "local administration" means administration (i.e., by a subcutaneous, intramuscular, subdermal, or transdermal route) of a pharmaceutical agent to or to the vicinity of a muscle or of a subdermal location or in the head of a patient by a non-systemic route. Thus, local administration excludes systemic (i.e., to the blood circulation system) routes of administration, such as intravenous or oral administration.

As used herein, the term "stress" refers to any physical, mental, or emotional factor that causes bodily or mental discomfort. Stress may manifest physically in a patient and thus may be measured or quantified in a variety of ways that are known in the medical field. Additionally or alternatively, stress may be measured through the information provided directly from a patient (e.g., patient surveys).

As used herein, the term "stress disorder" refers to a state of stress of a patient, measured in any of the ways known or understood in the art, that cannot be managed by the patient and is incapable of resolution on its own. Stress disorders may include, for example, post-traumatic stress disorder and acute stress disorder.

The term "post-traumatic stress disorder" ("PTSD") refers to a diagnosable stress disorder that is typically triggered by a stressful event. The psychological effects of this condition can include flashbacks, nightmares and severe anxiety, as well as uncontrollable thoughts about the event. However, as discussed herein, it is well understood in the field that it is possible for this condition to manifest physically in a patient as well.

The term "acute stress disorder" ("ASD") refers to a diagnosable stress disorder that typically begins immediately after a stressful or traumatic event and can last for several days to a month.

As used herein, "perceived stress" refers to the feelings or thoughts an individual has as to the amount of stress they are experiencing at a given point in time, or over a given period of time. Likewise, the term "perceived stress scale," refers to the numerical scale used to measure levels of perceived stress in an individual and is based on their completion of stress-related questions. For each question, the individual will report a numerical level of stress, typically between 0 and 4. A score is determined by adding the numbers given for each question. A lower overall score indicates lower levels of stress and higher overall scores indicates higher levels of stress.

The term "facial expression," as used herein, refers to a facial output that results from the summation of individual facial muscles being in a contracted or relaxed state at a given point in time.

As used herein, the term "composition" refers to a pharmaceutical preparation for administration to an intended subject for therapeutic purposes that contains at least one pharmaceutically active compound. The composition may include at least one pharmaceutically acceptable component to provide an improved formulation of the compound, such as a suitable carrier or excipient.

As used herein, the term "subject" refers to a living organism that is treated with compounds as described herein, including, for example, a human.

Methods

Stress-related disorders often manifest in individuals experiencing long-term anxiety due to psychological or physiological stress. Chronic stress conditions, such as PTSD, demonstrably have a negative impact on physical health and can increase the risk of cardiovascular disease, diabetes, and immune system complications. Moreover, chronic stress conditions can also lead to increased facial muscle activity. For instance, it is understood that stress disorders can lead to temporomandibular joint (TMJ) disorders and bruxism (i.e., oral parafunctional activity including grinding teeth and jaw clenching, etc.). In addition to TMJ disorders, elevated stress can lead to muscle twitching of the face, particularly in the muscles surrounding the eyes, forehead, and mouth.

The relationship between stress and increased facial muscle activity is more complex than once believed. Indeed, artificial manipulation of one's facial muscle activity can lead to lower stress levels in that individual. For example, individuals that smile while completing particularly stressful tasks have lower heartrates and report a more positive outlook when compared to non-smiling individuals completing the same stressful tasks. See Kraft and Pressman, *Grin and Bear it: The Influence of Manipulated Facial Expression on the Stress Response,* 23(11) APS 1372-78 (2012). In addition, positive social cues, such as smiling and other facial expressions associated with happiness, have been associated with activating the brain's reward system (e.g., dopaminergic, glutamatergic, and GABAergic pathways), which can influence an individual's overall mood and stress response. See Meier I. M. et al., *Naltexone Increases Negatively-Valenced Facial Responses to Happy Faces in Female Participants,* 74 PSYCHONEUROENDOCRINOLOGY 65-68 (2016).

Embodiments of the present disclosure relate to methods of treating stress and/or a stress condition in a patient through the use of an acetylcholine release inhibitor, such as a neurotoxic protein (e.g., a botulin toxin). In particular, the methods for treating stress in a patient described herein include administering an effective amount of a botulinum toxin to one or more muscles in a face of a patient to manipulate facial muscle activity in a manner that affects a facial expression and/or relieves muscle tension that results in positive feedback to the patient.

The methods disclosed herein may be used to treat stress in a patient. In embodiments of the invention, treating stress comprises reducing one or more symptoms of stress. Symptoms of stress that may be alleviated or reduced by various embodiments recited herein include, but are not limited to, the following: increased perspiration; increased heartrate; pupil dilation; low energy; headaches; migraines; digestive problems including upset stomach, diarrhea, constipation, and nausea; insomnia; frequent colds and infections; impotence; irritability; change in appetite; rapid weight loss; rapid weight gain; nail biting; fidgeting; pacing; increased use of alcohol and/or cigarettes; dry mouth; clenched jaw; teeth grinding; muscle twitches; anxiety; constant worrying; racing thoughts; inability to focus; nightmares and/or night terrors. It is understood that the list of symptoms provided is not exhaustive, and that one or more additional symptoms of stress not recited herein may be treated by various embodiments of the instant disclosure.

In embodiments of the invention, the methods disclosed herein may be used to treat a stress disorder, including for example, PTSD and/or ASD. ASD and PTSD are closely related, but clinically distinct mental disorders that can cause a range of psychological symptoms in a patient. ASD typically arises immediately after the traumatic event (e.g., within 1-3 days), and can lead to PTSD if left untreated. Symptoms of ASD include intrusion symptoms (i.e., feelings of being unable to stop reliving a traumatic event through flashbacks and vivid memories), dissociative symptoms (i.e., feelings of an altered reality or lack of awareness of surrounding), avoidance symptoms (i.e., purposefully avoiding people or places associated with the traumatic event), and symptoms of constant arousal including insomnia, irritability, and aggression. Individuals with PTSD experience similar symptoms, but also may experience various other behavioral and psychological symptoms including unwanted nightmares, severe anxiety, emotional detachment, and self-destructive behavior.

In certain embodiments of the invention, the methods disclosed herein may be used to alleviate an individual's perceived stress, such that their thoughts as to the amount of stress they are experiencing at a given point in time, or over a given period of time, are more positive. For example, in certain embodiments of the invention, the methods described herein may be used to alleviate one or more symptoms of stress in an individual such that the individual's score on the perceived stress scale is reduced when compared to their baseline score (i.e., the score reported for that individual before receiving treatment).

One or more of the methods for treating stress disclosed herein include manipulating facial muscle activity. In certain embodiments of the invention, manipulating facial muscle activity includes controlling the contraction of one or more facial muscles in a manner that affects a facial expression.

In certain embodiments of the invention, manipulating facial muscle activity includes controlling the contraction of one or more facial muscles in a manner that relieves tension in the muscle. The facial muscles are a group of approximately 43 striated muscles that are used to control necessary functions for daily life including mastication and facial expression. See Westbrook K. E. and Varacello M., *Anatomy, Head and Neck, Facial Muscles*, STATPEARLS (2019). Facial muscles originate on the surface of the skull and insert to fibers that are intertwined with connective tissue and the dermis of the skin. It is because of this insertion with connective tissue and skin that the muscles are able to control facial expressions upon their contraction and relaxation. In embodiments, facial muscles that may be manipulated include the orbicularis oculi, nasalis, levator labii superioris alaeque nasi, depressor labii inferioris, procerus, auriculars, zygomaticus major, zygomaticus minor, buccinator, occipitofrontalis (including the frontal and occipital belly), corrugator supercilii, risorius, depressor anguli oris, orbicularis oris, mentalis, temporalis, medial pterygoid, lateral pterygoid, and the masseter.

In embodiments of the invention, manipulating facial muscle activity includes controlling the contraction of one or more facial muscles in a manner dependent on their function and location. In certain embodiments of the invention, manipulating facial muscle activity to control the contraction of one or more facial muscles in a manner dependent on their function and location affects a facial expression. For example, in certain embodiments of the invention, manipulating the activity of one or more of the facial muscles that control the mouth may affect a facial expression in a manner that results in a smile or grin. In certain embodiments of the invention, manipulating the activity of one or more facial muscles that control the mouth may affect a facial expression in a manner that results in the prevention of a frown or pursed lips. In embodiments of the invention, facial expressions may include, for example, happiness, excitement, anger, frustration, fear, and sadness. Manipulating facial muscle activity to affect a facial expression results in positive feedback to the patient in a manner that alleviates stress.

In embodiments of the invention, manipulating facial muscle activity to control the contraction of one or more facial muscles in a manner dependent on their function and location relieves tension in the muscle or muscles manipulated. For example, in certain embodiments of the invention, manipulating facial muscle activity to control the contraction of the masseter muscle relieves tension in the muscle. Loss of tension in the masseter creates a positive feedback mechanism in the patient resulting in the alleviation of stress.

In embodiments of the invention, facial muscles that are associated with the mouth and whose activity may be manipulated include the levator labii superioris, depressor labii inferioris, depressor angulus oris, zygomaticus major, zygomaticus minor, orbicularis oris, buccinator, risorius, and the mentalis. For example, the orbicularis oris is a circular facial muscle that controls the lips, including controlling their shape during speech and at rest (i.e., when not speaking). In certain embodiments of the invention, manipulating the activity of the orbicularis oris affects a facial expression. In certain embodiments of the invention, a facial expression that may be affected by manipulating the activity of the orbicularis oris includes frowning. In certain embodiments of the invention, the activity of other facial muscles associated with the mouth may be manipulated to affect a facial expression. For example, in embodiments of the invention, the activity of the depressor anguli oris and platysma may be manipulated to affect a facial expression. In certain embodiments of the invention, a facial expression that may be affected by manipulating the activity of the depressor anguli oris and platysma includes frowning. In certain embodiments of the invention, manipulating the activity of the orbicularis oris, depressor anguli oris, and/or platysma relieves tension in these muscles.

It is to be understood that the activity of all facial muscles that control the mouth disclosed herein may be manipulated to affect a facial expression and/or relieve tension in even if not specifically mentioned.

In embodiments of the invention, the activity of the muscles associated with the mouth and other facial muscles, including those that are associated with the eyes, nose, and brow, may be manipulated either individually or collectively to affect a facial expression. For example, in certain embodiments of the invention, the activity of the facial muscles associated with the brow, including the occipitofrontalis, procerus, and corrugator supercilii, may be manipulated to affect a facial expression. The occipitofrontalis is a large facial muscle that consists of two parts including the occipital belly and the frontal belly. Both bellies operate to draw the scalp back resulting in the raising of the eyebrows and the wrinkling of the forehead. The corrugator supercilii and procerus are pyramid-shaped muscles that functions to draw the eyebrow downward and medially. In certain embodiments of the invention, manipulating the activity of the occipitofrontalis, procerus, and/or corrugator supercilii affects a facial expression. In certain embodiments, a facial expression that may be affected by manipulating the activity of the occipitofrontalis and/or corrugator supercilii includes scowling or frowning. In certain embodiments of the invention, other facial muscles that control the brow, including those of the glabellar complex (e.g., depressor supercilii and orbital orbicularis) may be manipulated to affect a facial expression.

In certain embodiments of the invention, muscles associated with the eyes, nose, and brow, may be manipulated either individually or collectively to relieve tension in the targeted muscles. For example, in certain embodiments of the invention, the activity of the facial muscles associated with the brow, including the occipitofrontalis, procerus, and corrugator supercilii, may be manipulated to relieve tension.

In certain embodiments of the invention, the activity of the facial muscles associated with the nose may be manipulated to affect a facial expression. For example, the nasalis is a sphincter-like facial muscle whose function is to compress nasal cartilages and is the facial muscle primarily responsible for flaring the nostrils. In certain embodiments of the invention, manipulating the activity of the nasalis affects a facial expression. In some embodiments of the invention, a facial expression that may be affected includes scowling or disgust.

In embodiments of the invention, the activity of the facial muscles associated with the nose may be manipulated to relieve tension in the targeted muscles. For example, tension in the nasalis may be relieved by manipulating the activity of the nasalis.

In embodiments of the invention, the activity of the facial muscles associated with the eyes, including those that surround the eyes, may be manipulated. For example, in certain embodiments of the invention, the activity of the orbicularis oculi may be manipulated. The orbicularis oculi is a facial muscle that functions to close the eyelids. In embodiments of the invention, manipulating the activity of the orbicularis oculi affects a facial expression. In certain embodiments of the invention, a facial expression that may be affected by manipulating the activity of the orbicularis oculi includes anger or frustration. In embodiments of the invention, other facial muscles associated with the eyes including, for example, the corrugator supercilii, may be manipulated in to affect a facial expression.

In embodiments of the invention, the activity of the facial muscles associated with the eyes may be manipulated to relieve tension in the targeted muscle. For example, tension to the corrugator supercilii may be relieved by manipulating the activity of the corrugator supercilii.

It is to be understood that the activity of all facial muscles disclosed herein, including those that control the eyes, nose, brow, and mouth may be manipulated either individually, collectively, and/or combinatorially, to affect a facial expression, even if not specifically identified. Moreover, it is to be understood that the activity of all facial muscles disclosed herein, including those that control the eyes, nose, brow, and mouth may be manipulated either individually, collectively, and/or combinatorially, to relieve tension in the targeted muscle or muscles. For example, in embodiments of the invention, the activity of the depressor anguli oris, platysma, zygomaticus major, zygomaticus minor, corrugators, procerus, orbicularis oculi, *frontalis*, risorius, masseter, temporalis, and occipitalis may be manipulated individually, collectively, and/or combinatorially to affect a facial expression and/or to relieve tension.

It is also to be understood that the facial muscles associated with a specific facial feature (e.g., the mouth, nose, eyes, and brow) are not exclusively tied that that facial feature and may control more than one expression associated with other facial features. For example, the corrugator supercilii is associated with both the eyes and brow and, therefore, may be manipulated by various embodiments disclosed herein to produce a facial expression that involves both of those groups of facial features.

In embodiments of the invention of the invention, a facial expression that may be affected by manipulating the activity of the facial muscles (i.e., manipulating the contraction and/or relaxation of the muscle) that control the eyes, nose, brow, and/or mouth include, for example, human facial expressions commonly associated with happiness, joy, excitement, anger, frustration, fear, confusion, disgust, and sadness. This list of facial expressions recited is not meant to be exhaustive and may include other facial expressions known in the art and/or specific to a given subject, as subjects may express emotions through differing facial expressions.

Manipulating facial muscle activity, as used by one or more of the embodiments described herein, includes controlling the contraction of one or more facial muscles. In certain embodiments of the invention, manipulating facial muscle activity affects a facial expression. In certain embodiments of the invention, manipulating facial muscle activity relieves tension in the targeted muscle. It is to be understood that manipulating facial muscle activity may simultaneously affect a facial expression and relieve tension in the targeted muscle or muscles.

In certain embodiments of the invention, manipulating facial muscle activity includes inducing the contraction of a facial muscle. For example, in certain embodiments of the invention, manipulating facial muscle activity may include applying an electric current to the muscle thereby inducing its contraction. In certain embodiments of the invention, manipulating facial muscle activity includes preventing the contraction of the facial muscle (i.e., inducing paresis of the muscle). In certain embodiments of the invention, manipulating facial muscle activity to prevent contraction of a facial muscle may include administering of an acetylcholine release inhibiting drug (e.g., botulinum toxin).

In certain embodiments of the invention, manipulating facial muscle activity is achieved through neurotoxin-mediated paresis. For example, in certain embodiments of the invention, a neurotoxin is administered to a patient to manipulate facial muscle activity. In embodiments of the invention, the neurotoxin is an acetylcholine release inhibiting neurotoxin. In certain embodiments of the invention, the acetylcholine release inhibiting neurotoxin is a *Clostridial* neurotoxin. The *Clostridium* genus of gram-positive bacteria produces several human pathogens including *Clostridium botulinum, Clostridium butyricum, Clostridium tetani, Clostridium perfringens, Clostridium sporogenes, Clostridium leptum, Clostridium difficile* and *Clostridium beratti*. Of those recited, *Clostridium botulinum* and *Clostridium tetani* produce neurotoxins and are the causative agents of botulism and tetanus, respectively. See Binz T. et al, *Clostridial* Neurotoxins: Mechanism of SNARE Cleavage and Outlook on Potential Substrate Specificity Reengineering, 2(4) TOXINS (BASEL), 665-82 (2010).

In certain embodiments of the invention, treating stress in a patient by manipulating their facial muscle activity includes administering an acetylcholine release inhibiting neurotoxin such as, for example, a botulinum toxin. Normally, the firing of an action potential releases acetylcholine from the cytosol of a pre-synaptic axon into the synapse to control muscle contraction in nearby muscle cells. Botulinum toxin, however, prevents the release of acetylcholine (among other neurotransmitters) into the synapse and thereby inhibits muscle contraction in affected cells and tissues. The effects from an intramuscular botulinum toxin injection can last for several months before it gradually begins to wear off. Seven immunologically distinct botulinum serotypes have been characterize, including types A, B, C, D, E, F and G. Despite its high toxicity, botulinum toxin is one of the most popular drugs to combat the external signs of facial aging and it is commercially available (e.g., BOTOX®, Dysport®, Xeomi®, and MyoBloc®) to treat ailments such as neuromuscular disorders (e.g., blepharospasm, synkinesis, cervical dystonia, strabismus, hemifacial spasms, and upper-limb spasticity) and headaches (e.g., migraines, sinus headaches, etc.). Id.

In embodiments of the invention, methods for alleviating one or more symptoms of stress includes administering a botulinum toxin to manipulate the facial muscle activity of a patient to affect a facial expression. In certain embodiments of the invention, methods for alleviating one or more symptoms of stress includes administering a botulinum toxin to manipulate the facial muscle activity of a patient to relieve tension in the targeted muscle.

In certain embodiments of the invention, manipulating the facial muscle activity of a patient by administering a botulinum toxin affects a facial expression resulting in the reduction of one or more symptoms of stress. In certain embodiments of the invention, manipulating the facial muscle activity of patient by administering a botulinum toxin relieves tension in the muscle resulting in the reduction of one or more symptoms of stress. Manipulating facial muscle activity to affect a facial expression of happiness, results in positive feedback to the patient, which in turn, alleviates stress in the patient. Manipulating facial muscle activity in a patient may also relieve tension in the muscle targeted, which in turn, results in positive feedback to the patient and alleviates stress.

In certain embodiments of the invention, the botulinum toxin may be selected from the group consisting of serotypes A, B, C, D, E, F, and G. In certain embodiments of the invention, the botulinum toxin may be type A, type B, type C, type D, type E, type F, type G or any combination thereof. In certain embodiments of the invention, the botulinum toxin may be a recombinantly made, (i.e., produced by $E.$ $coli$), modified (altering at least one amino acid), or it may comprise a derivative or fragment thereof.

The methods for treating stress described herein include administering a neurotoxin (e.g., botulinum toxin) to manipulate the facial muscle activity of a patient to affect a facial expression. In certain embodiments of the invention, the methods described herein include administering a neurotoxin to manipulate the facial muscle activity of a patient in a manner that relieves or reduces tension in the muscle. In embodiments of the invention, manipulating the facial muscle activity of a patient includes administering a neurotoxin to one or more muscles in a face of a patient. In certain embodiments of the invention, the neurotoxin may be administered by a transdermal route. In certain embodiments of the invention, a transdermal route of administration may include for example, a cream, a patch, a mask, a spray, a facewash, a gel, a lotion, or through any other vehicle a person or ordinary skill in the art would use to deliver a drug across the skin.

In certain embodiments of the invention, the neurotoxin is administered to one or more muscles in the face of a patient by injection. In certain embodiments of the invention, administration may include local injection of the neurotoxin to one or more muscles in a face of a patient. In certain embodiments of the invention, local injection of a neurotoxin to one or more facial muscles manipulates facial muscle activity to affect a facial expression. In certain embodiments of the invention, local injection of a neurotoxin to one or more facial muscles manipulates facial muscle activity in a manner that relieves tension in the muscle. In certain embodiments of the invention, local injection of a neurotoxin, including for example, a botulinum toxin, to one or more facial muscles affects a facial expression in a patient resulting in the alleviation of stress. In certain embodiments of the invention, local injection of a neurotoxin, such as a botulinum toxin, to one or more facial muscles manipulates facial muscle activity in a manner that relieves tension in the muscle or muscles thereby resulting in the alleviation of stress.

In embodiments of the invention, the neurotoxin may be administered by intramuscular injection. In certain embodiments of the invention, the neurotoxin may be administered by subcutaneous injection. In certain embodiments of the invention, the neurotoxin may be administered by intradermal injection.

In embodiments of the invention, administering a neurotoxin to manipulate the facial muscle activity of a patient includes administering an effective amount of the neurotoxin. The quantity of neurotoxin to be administered in accordance with the methods disclosed herein may vary depending on the patient, including their stress level and responsiveness to treatment. For botulinum toxin, the quantity to be administered in accordance with the methods disclosed herein may also depend on the brand of botulinum toxin to be administered (e.g., BOTOX®, Dysport®, Xeomin®, and MyoBloc®). In embodiments of the invention, the amount of botulinum toxin to be administered according to the methods disclosed herein is between about 1 unit and about 3,000 units. For example, in certain embodiments of the invention, the amount of botulinum toxin to be administered is between about 5 units and about 2,000 units, between about 10 units and about 1,500 units, between about 15 units and about 1,000 units, between about 20 units and about 500 units, between about 25 units and about 300 units, between about 30 units and about 200 units, between about 35 units and about 100 units, between about 40 units and about 70 units, or between about 50 units and about 60 units. In embodiments, the botulinum toxin may be selected from the group consisting of botulinum toxin types A, B, C, D, E, F, and G. In certain embodiments of the invention, the botulinum toxin is type A and is administered to one or more muscles in the face of a patient in an amount between about 1 and about 1,000 units.

The methods for treating stress in a patient described herein include administering an effective amount of a botulinum toxin to one or more muscles in a face of a patient to manipulate their facial muscle activity. In certain embodiments of the invention, treating stress in a patient includes administering an effective amount of a botulinum toxin to one or more muscles to affect a facial expression. In certain embodiments of the invention, treating stress in a patient includes administering an effective amount of a botulinum toxin in a manner that relieves or reduces tension in the targeted muscle or muscles.

In certain embodiments of the invention, the stress that may be treated through administering an effective amount of a botulinum toxin into one or more muscles in a face of a patient to manipulate their facial muscle activity to affect a facial expression includes, for example, PTSD. In certain embodiments of the invention, the stress that may be treated through administering an effective amount of a botulinum toxin into one or more muscles in a face of a patient to manipulate their facial muscle activity to relieve tension in the muscle or muscles includes, for example, PTSD.

In certain embodiments of the invention, the stress that may be treated through administering an effective amount of a botulinum toxin into one or more muscles in a face of a patient to manipulate their facial muscle activity to affect a facial expression includes, for example, perceived stress. In certain embodiments of the invention, the stress that may be treated through administering an effective amount of a botulinum toxin into one or more muscles in a face of a patient to manipulate their facial muscle activity to relieve tension in the targeted muscle or muscles includes, for example, perceived stress.

In embodiments of the invention, treating or alleviating stress in a patient includes manipulating the activity of one or more muscles in a patient's face by administering an effective amount of a botulinum toxin, for example botulinum toxin type A, to affect a facial expression. In certain embodiments of the invention, the facial muscles whose activity may be influenced by manipulation include the corrugator supercilii, procerus, depressor supercilii, orbicularis oculi, *frontalis*, masseter, depressor anguli oris, temporalis, and the platysma. In certain embodiments of the invention, administration of the botulinum toxin is by local injection. In certain embodiments of the invention, the amount of botulinum toxin type A to be injected is between about 1 unit and about 50 units per injection.

In embodiments of the invention, treating or alleviating stress in a patient includes manipulating the activity of one or more muscles in a patient's face by administering an effective amount of a botulinum toxin, for example botulinum toxin type A, in a manner that relieves tension in the targeted muscle. In certain embodiments of the invention, the facial muscles whose activity may be influenced by manipulation include the corrugator supercilii, procerus, depressor supercilii, orbicularis oculi, *frontalis*, masseter, depressor anguli oris, temporalis, and the platysma. In certain embodiments of the invention, administration of the botulinum toxin is by local injection. In certain embodiments of the invention, the amount of botulinum toxin type A to be injected is between about 1 unit and about 50 units per injection.

Other objectives, features and advantages of the present invention will become apparent from the following examples. The specific examples, while indicating specific embodiments of the invention, are provided by way of illustration only. Accordingly, the present invention also includes those various changes and modifications within the spirit and scope of the invention that may become apparent to those skilled in the art from this detailed description. The invention will be further illustrated by the following non-limiting examples.

Prophetic Example 1

A prospective observational study will be performed to determine if patients receiving onabotulinumtoxinA (e.g., BOTOX®) injections experience any alleviation or decrease in one or more symptoms of stress, including perceived levels of stress. It is hypothesized that patients receiving local injections of onabotulinumtoxinA will experience a decrease in one or more symptoms of stress, including lower scores on the perceived stress scale.

Number of patients: 60 subjects, 30 subjects per arm.

Patient Population: The patient population will include patients between the ages of 40-65, who score moderate to severe on the perceived stress scale. Patients will be randomized to receive either placebo injections or onabotulinumtoxinA injections.

Injection Scheme:

| Facial Muscle | Dose (Units)/Injection | Total Injections |
| --- | --- | --- |
| Glabellar complex | 25 | 5 |
| Occipitofrontalis | 30 | 10 |
| Masseter | 40 | 6 |
| Depressor anguli oris | 20 | 4 |
| Platysma | 50 | 14 |

Primary Endpoint: It is hypothesized that the patients receiving local injections of onabotulinumtoxinA injections proximal to the glabellar complex (e.g., corrugator supercilii, procerus, depressor supercilii, and the orbicularis oculi), depressor anguli oris, platysma, occipitofrontalis (both the frontal and occipital bellies), and the masseter facial muscles will experience a decrease in one or more symptoms of stress, including perceived levels of stress from baseline.

Study Duration: Patients will receive one onabotulinumtoxinA injection (or placebo injection) and will be monitored over a 26 week period with follow up appoints after the first injection at two-weeks, with monthly follow-ups once a month for the next 5 months (total of 6 months).

Prophetic Example 2

A prospective observational study will be performed to determine if patients receiving onabotulinumtoxinA (e.g., BOTOX®) injections experience any alleviation or decrease in one or more symptoms of stress, including perceived levels of stress. It is hypothesized that patients receiving local injections of onabotulinumtoxinA will experience a decrease in one or more symptoms of stress, including lower scores on the perceived stress scale.

Number of patients: 20 subjects, 15 patients in the onabotulinumtoxinA arm and 5 patients in the placebo arm.

Patient Population: The patient population will include patients between the ages of 40-65, who score moderate to severe on the perceived stress scale. Patients will be randomized to receive either placebo injections or onabotulinumtoxinA injections.

Injection Scheme:

| Facial Muscle | Dose (Units)/Injection | Total Injections |
| --- | --- | --- |
| Glabellar complex | 25 | 5 |
| Occipitofrontalis | 30 | 10 |
| Masseter | 40 | 6 |
| Depressor anguli oris | 20 | 4 |
| Platysma | 50 | 14 |

Primary Endpoint: It is hypothesized that the patients receiving onabotulinumtoxinA injections proximal to the glabellar complex (e.g., corrugator supercilii, procerus, depressor supercilii, and the orbicularis oculi), depressor anguli oris, platysma, occipitofrontalis (both the frontal and occipital bellies), and the masseter facial muscles will experience a decrease in one or more symptoms of stress, including perceived levels of stress from baseline.

Study Duration: Patients will receive one onabotulinumtoxinA injection (or placebo injection) and will be monitored over a 26 week period with follow up appoints after the first injection at two-weeks, with monthly follow-ups once a month for the next 5 months (total of 6 months).

Prophetic Example 3

A prospective observational study will be performed to determine if patients receiving onabotulinumtoxinA (e.g., BOTOX®) injections experience any alleviation or decrease in one or more symptoms of a stress disorder, including for example, PTSD. It is hypothesized that patients receiving local injections of onabotulinumtoxinA will experience a decrease in one or more symptoms of stress associated with PTSD.

Number of patients: 60 subjects, 30 patients in each arm.

Patient Population: The patient population will include patients between the ages of 20-65 that are diagnosed with PTSD. Patients will be randomized to receive either placebo injections or onabotulinumtoxinA injections.

Injection Scheme:

| Facial Muscle | Dose (Units)/Injection | Total Injections |
| --- | --- | --- |
| Glabellar complex | 25 | 5 |
| Occipitofrontalis | 30 | 10 |
| Masseter | 40 | 6 |
| Depressor anguli oris | 20 | 4 |
| Platysma | 50 | 14 |

Primary Endpoint: It is hypothesized that the patients receiving onabotulinumtoxinA injections proximal to the glabellar complex (e.g., corrugator supercilii, procerus, depressor supercilii, and the orbicularis oculi), depressor anguli oris, platysma, occipitofrontalis (both the frontal and occipital bellies), and the masseter facial muscles will experience a decrease in one or more symptoms of PTSD.

Study Duration: Patients will receive one onabotulinumtoxinA injection (or placebo injection) and will be monitored over a 26 week period with follow up appoints after the first injection at two-weeks, with monthly follow-ups once a month for the next 5 months (total of 6 months).

It is understood that the present invention is not limited to the specific details of these examples. While a preferred embodiment of the invention has been shown and described in considerable detail, it should be understood that many changes can be made in the structure without departing from the spirit or scope of the invention. Accordingly, it is not desired that the invention should be limited to the exact structure shown and described.

What is claimed is:

1. A method of treating a stress disorder, the method comprising:
    administering an effective amount of an acetylcholine release inhibiting neurotoxin to an occipitofrontalis of a patient in need thereof.

2. The method of claim 1, wherein the acetylcholine release inhibiting neurotoxin is a *Clostridial* toxin.

3. The method of claim 2, wherein the *Clostridial* toxin is a botulinum toxin.

4. The method of claim 3, wherein the botulinum toxin is any one of the following types:
    type A, type B, type C, type D, type E, or type G.

5. The method of claim 4, wherein the acetylcholine release inhibiting neurotoxin is administered to the patient transdermally, subdermally, or intradermally.

6. The method of claim 5, wherein the acetylcholine release inhibiting neurotoxin is further administered to one or more muscles in a face of the patient selected from the group consisting of auriculars, buccinator, corrugator, corrugator procerus, corrugator, supercilia, depressor anguli oris, depressor labii inferioris, depressor supercilii, *frontalis*, lateral pterygoid, levator labii superioris alaeque nasi, masseter, medial pterygoid, mentalis, nasalis, occipitalis, orbicularis oculi, orbicularis oris, platysma, procerus, risorius, supercilia, temporalis, zygomaticus major, and zygomaticus minor.

7. The method of claim 1, wherein the acetylcholine release inhibiting neurotoxin is further administered to one or more muscles in a face of the patient selected from the group consisting of auriculars, buccinator, corrugator, corrugator procerus, corrugator, supercilia, depressor anguli oris, depressor labii inferioris, depressor supercilii, *frontalis*, lateral pterygoid, levator labii superioris alaeque nasi, masseter, medial pterygoid, mentalis, nasalis, occipitalis, orbicularis oculi, orbicularis oris, platysma, procerus, risorius, supercilia, temporalis, zygomaticus major, and zygomaticus minor.

8. The method of claim 1, wherein the acetylcholine release inhibiting neurotoxin is further administered to a corrugator, a procerus, an orbicularis oculi, a depressor anguli oris, a platysma, an occipitofrontalis, and a masseter.

9. The method of claim 1, wherein the acetylcholine release inhibiting neurotoxin is further administered to a glabellar complex, a masseter, a depressor anguli oris, and a platysma.

10. A method of treating post-traumatic stress disorder, the method comprising:
    administering an effective amount of an acetylcholine release inhibiting neurotoxin to an orbicularis oculi of a patient in need thereof.

11. The method of claim 10, wherein the acetylcholine release inhibiting neurotoxin is a *Clostridial* toxin.

12. The method of claim 11, wherein the *Clostridial* toxin is a botulinum toxin.

13. The method of claim 12, wherein the botulinum toxin is any one of the following types:
    type A, type B, type C, type D, type E, or type G.

14. The method of claim 13, wherein the acetylcholine release inhibiting neurotoxin is administered to the patient transdermally, subdermally, or intradermally.

15. The method of claim 14, wherein the acetylcholine release inhibiting neurotoxin is further administered to one or more muscles of the patient selected from the group consisting of auriculars, buccinator, corrugator, corrugator procerus, corrugator, supercilia, depressor anguli oris, depressor labii inferioris, depressor supercilii, *frontalis*, lateral pterygoid, levator labii superioris alaeque nasi, masseter, medial pterygoid, mentalis, nasalis, occipitalis, occipitofrontalis, orbicularis oris, platysma, procerus, risorius, supercilia, temporalis, zygomaticus major, and zygomaticus minor.

16. The method of claim 10, wherein the acetylcholine release inhibiting neurotoxin is further administered to one or more muscles of the patient selected from the group consisting of auriculars, buccinator, corrugator, corrugator procerus, corrugator, supercilia, depressor anguli oris, depressor labii inferioris, depressor supercilii, *frontalis*, lateral pterygoid, levator labii superioris alaeque nasi, masseter, medial pterygoid, mentalis, nasalis, occipitalis, occipitofrontalis, orbicularis oris, platysma, procerus, risorius, supercilia, temporalis, zygomaticus major, and zygomaticus minor.

17. The method of claim 10, wherein the acetylcholine release inhibiting neurotoxin is further administered to a corrugator, a procerus, a depressor anguli oris, a platysma, a *frontalis*, and a masseter.

* * * * *